United States Patent
Mitchell

(10) Patent No.: US 11,185,565 B2
(45) Date of Patent: Nov. 30, 2021

(54) COMPOSITIONS INCLUDING MILK THISTLE AND METHODS OF USE

(71) Applicant: GM Pharmaceuticals, Inc., Arlington, TX (US)

(72) Inventor: Odes W. Mitchell, Arlington, TX (US)

(73) Assignee: GM Pharmaceuticals, Inc., Fort Worth, TX (US)

( * ) Notice: Subject to any disclaimer, the term of this patent is extended or adjusted under 35 U.S.C. 154(b) by 4 days.

(21) Appl. No.: 16/731,928

(22) Filed: Dec. 31, 2019

(65) Prior Publication Data

US 2020/0206290 A1 Jul. 2, 2020

Related U.S. Application Data

(60) Provisional application No. 62/787,652, filed on Jan. 2, 2019.

(51) Int. Cl.
| | | |
|---|---|---|
| *A61K 36/00* | (2006.01) | |
| *A61K 36/28* | (2006.01) | |
| *A61K 36/54* | (2006.01) | |
| *A61K 9/00* | (2006.01) | |
| *A61K 31/4375* | (2006.01) | |
| *A61K 33/24* | (2019.01) | |

(52) U.S. Cl.
CPC ............ *A61K 36/28* (2013.01); *A61K 9/0053* (2013.01); *A61K 31/4375* (2013.01); *A61K 33/24* (2013.01); *A61K 36/54* (2013.01)

(58) Field of Classification Search
None
See application file for complete search history.

(56) References Cited

U.S. PATENT DOCUMENTS

| | | | | |
|---|---|---|---|---|
| 8,993,008 B1 * | 3/2015 | Mashat | .................. | A61K 36/51 424/725 |
| 2010/0093780 A1 * | 4/2010 | Sumi | ........................ | A23G 4/12 514/292 |
| 2016/0166631 A1 * | 6/2016 | Liu | ........................ | A61K 9/209 424/455 |

OTHER PUBLICATIONS

Di Pierro, Preliminary study about the possible glycemic clinical advantage in using a fixed combination of Berberis aristata and Silybum marianum standardized extracts in patients with type 2 diabetes. Clinical pharmacology : advances and applications, (2013) vol. 5, pp. (Year: 2013).*

Rao, Efficacy of berberine hydrochloride on biochemical parameters in Indian type 2 diabetic patients. Endocrine Practice, (Jan. 2017) vol. 23, No. 1, pp. 18A (Year: 2017).*

* cited by examiner

*Primary Examiner* — Qiuwen Mi
(74) *Attorney, Agent, or Firm* — Winstead PC

(57) ABSTRACT

In an embodiment, the present disclosure pertains to a dietary supplement including berberine in an amount up to about 1500 mg, cinnamon in an amount up to about 300 mg, chromium in an amount up to about 300 mcg, milk thistle in an amount up to about 150 mg, and pyrroloquinoline quinone disodium (PQQ) in an amount up to about 30 mg. Additionally, the present disclosure relates to a method for managing weight, maintaining healthy blood sugar levels, preventing diabetes, or alleviating symptoms associated with diabetes, including administering a composition to a subject. In some embodiments, the composition includes berberine in an amount up to about 1500 mg, cinnamon in an amount up to about 300 mg, chromium in an amount up to about 300 mcg, milk thistle in an amount up to about 150 mg, and PQQ in an amount up to about 30 mg.

33 Claims, No Drawings

COMPOSITIONS INCLUDING MILK THISTLE AND METHODS OF USE

CROSS-REFERENCE TO RELATED APPLICATIONS

This patent application claims priority from, and incorporates by reference the entire disclosure of, U.S. Provisional Application No. 62/787,652 filed on Jan. 2, 2019.

TECHNICAL FIELD

The present disclosure relates generally to milk thistle and more particularly, but not by way of limitation, to compositions including milk thistle and methods of use.

BACKGROUND

This section provides background information to facilitate a better understanding of the various aspects of the disclosure. It should be understood that the statements in this section of this document are to be read in this light, and not as admissions of prior art.

Excess weight has reached epidemic proportions globally, with more than one billion adults being either overweight or obese. This number has more recently increased to more than two billion people. Additionally, these increases have been observed across all age groups. The more excess weight an individual has the more resistant their muscle and tissue cells become to their own insulin hormone and this can lead to diabetes. Dietary supplements are beneficial for improving overall health and for managing various aspects of health, for example, weight and blood sugar levels.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure relates to a dietary supplement including berberine in an amount up to about 1500 mg, cinnamon in an amount up to about 300 mg, chromium in an amount up to about 300 mcg, milk thistle in an amount up to about 150 mg, and pyrroloquinoline quinone disodium (PQQ) in an amount up to about 30 mg. In some embodiments, the berberine is in a range of about 62.5 mg to about 437.5 mg, the cinnamon is in a range of about 12.5 mg to about 87.5 mg, the chromium is in a range of about 12.5 mcg to about 87.5 mcg, the milk thistle is in a range of about 6.25 mg to about 43.75 mg, and the PQQ is in a range of about 1.25 mg to about 8.75 mg. In some embodiments, the berberine is in a range of about 125 mg to about 375 mg, the cinnamon is in a range of about 25 mg to about 75 mg, the chromium is in a range of about 25 mcg to about 75 mcg, the milk thistle is in a range of about 12.5 mg to about 37.5 mg, and the PQQ is in a range of about 2.5 mg to about 7.5 mg. In some embodiments, the berberine is in a range of about 187.5 mg to about 312.5 mg, the cinnamon is in a range of about 37.5 mg to about 62.5 mg, the chromium is in a range of about 37.5 mcg to about 62.5 mcg, the milk thistle is in a range of about 18.75 mg to about 31.25 mg, and the PQQ is in a range of about 3.75 mg to about 6.25 mg.

In some embodiments, the berberine is about 250 mg. In some embodiments, the berberine is about 500 mg. In some embodiments, the cinnamon is about 50 mg. In some embodiments, the chromium is about 50 mcg. In some embodiments, the milk thistle is about 25 mg. In some embodiments, the PQQ is about 5 mg. In some embodiments, the berberine can include, without limitation, berberine HCl, a berberine salt, or combinations thereof. In some embodiments, the berberine is berberine HCl. In some embodiments, the cinnamon can include, without limitation, Ceylon cinnamon, *Cassia* cinnamon, Korintje cinnamon, Padang *Cassia* cinnamon, Indonesian cinnamon, Saigon cinnamon, Vietnamese *Cassia* cinnamon, Vietnamese cinnamon, Malabar cinnamon, Indian cinnamon, or combinations thereof. In some embodiments, the cinnamon is Ceylon cinnamon. In some embodiments, the chromium can include, without limitation, chromium picolinate, chromium chloride, chromium aspartate, chromium amino acid chelate, chromium nicotinate (polynicotinate), glucose tolerance factor chromium, or combinations thereof. In some embodiments, the dietary supplement is in a form of a pharmaceutical carrier that can include, but is not limited to, a tablet, a capsule, an extended release tablet, an extended release capsule, a liquid, a suspension, a powder, a softgel, or combinations thereof.

In another embodiment, the present disclosure relates to a method for managing weight, maintaining healthy blood sugar levels, preventing diabetes, or alleviating symptoms associated with diabetes. In some embodiments, the method includes administering a composition to a subject. In some embodiments, the composition includes berberine in an amount up to about 1500 mg, cinnamon in an amount up to about 300 mg, chromium in an amount up to about 300 mcg, milk thistle in an amount up to about 150 mg, and PQQ in an amount up to about 30 mg. In some embodiments, the berberine is in a range of about 62.5 mg to about 437.5 mg, the cinnamon is in a range of about 12.5 mg to about 87.5 mg, the chromium is in a range of about 12.5 mcg to about 87.5 mcg, the milk thistle is in a range of about 6.25 mg to about 43.75 mg, and the PQQ is in a range of about 1.25 mg to about 8.75 mg. In some embodiments, the berberine is in a range of about 125 mg to about 375 mg, the cinnamon is in a range of about 25 mg to about 75 mg, the chromium is in a range of about 25 mcg to about 75 mcg, the milk thistle is in a range of about 12.5 mg to about 37.5 mg, and the PQQ is in a range of about 2.5 mg to about 7.5 mg. In some embodiments, the berberine is in a range of about 187.5 mg to about 312.5 mg, the cinnamon is in a range of about 37.5 mg to about 62.5 mg, the chromium is in a range of about 37.5 mcg to about 62.5 mcg, the milk thistle is in a range of about 18.75 mg to about 31.25 mg, and the PQQ is in a range of about 3.75 mg to about 6.25 mg.

In some embodiments, the berberine is about 250 mg. In some embodiments, the berberine is about 500 mg. In some embodiments, the cinnamon is about 50 mg. In some embodiments, the chromium is about 50 mcg. In some embodiments, the milk thistle is about 25 mg. In some embodiments, the PQQ is about 5 mg. In some embodiments, the berberine is can include, without limitation, berberine HCl, a berberine salt, or combinations thereof. In some embodiments, the berberine is berberine HCl. In some embodiments, the cinnamon can include, without limitation, Ceylon cinnamon, *Cassia* cinnamon, Korintje cinnamon, Padang *Cassia* cinnamon, Indonesian cinnamon, Saigon cinnamon, Vietnamese *Cassia* cinnamon, Vietnamese cinnamon, Malabar cinnamon, Indian cinnamon, or combinations thereof. In some embodiments, the cinnamon is Ceylon cinnamon. In some embodiments, the chromium can include, without limitation, chromium picolinate, chromium chloride, chromium aspartate, chromium amino acid chelate, chromium nicotinate (polynicotinate), glucose tolerance factor chromium, or combinations thereof. In some embodiments, the composition is in a form of a pharmaceutical carrier that can include, but is not limited to, a tablet, a capsule, an extended release tablet, an extended release capsule, a liquid, a suspension, a powder, a softgel, or combinations thereof. In some embodiments, the composition is administered orally. In some embodiments, the composition is administered up to three times daily. In some embodiments, the composition is administered orally via two tablets three times daily. In some embodiments, the composition is administered orally via two tablets two times daily.

In a further embodiment, the present disclosure relates to a dietary supplement that includes berberine in an amount of about 250 mg, Ceylon cinnamon in an amount of about 50 mg, chromium in an amount of about 50 mcg, milk thistle in an amount of about 25 mg, and PQQ in an amount of about 5 mg.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

A healthy individual requires a minimum amount of fat for the proper function of the hormonal, reproductive, and immune systems, as thermal insulation, as shock absorption for sensitive areas, and as energy for future use. However, the accumulation of too much storage fat can impair movement, flexibility, and alter the appearance of the body. Moreover, being overweight, or affected by obesity, greatly increases the risk of developing diabetes, heart disease, stroke, fatty liver disease, kidney disease, and other health issues. As such, the present disclosure relates generally to dietary supplements for oral administration to support weight management and help maintain healthy blood sugar levels.

In certain embodiments, the present disclosure is directed to dietary supplements with active ingredients to promote weight management and healthy blood sugar levels. In various embodiments, the dietary supplement can be taken once daily or up to three times daily. Additional embodiments allow for higher doses per day. The dietary supplements disclosed herein include a combination of unique compounds that were specifically chosen and combined according to their biological and physiological activities. Each compound disclosed herein can be used in combination to significantly help manage weight and blood sugar levels. Described herein are advanced formulas for milk thistle dietary supplements with a combination of other supplements and/or compounds. As such, the compositions of the dietary supplements disclosed herein can help prevent diabetes and/or alleviate symptoms associated with diabetes, and further, provide assistance in weight loss and weight management.

Milk thistle has shown high potential to help maintain healthy blood sugar levels in an individual, and has been the focus of many studies researching the potential benefits of milk thistle. A particular study found that using milk thistle, in addition to diabetes medication, helped individuals maintain healthy blood sugar levels. This particular study also demonstrated that milk thistle helped individuals lose weight and decrease their body mass index over the course of 120 days, compared to using diabetes medication alone. Research also demonstrates that milk thistle has a laxative effect, which results in water weight loss, and can thus be used to control and/or lose weight.

According to various studies, milk thistle helps lower blood sugar levels, especially when used as a complementary supplement with diabetes medication. It has been demonstrated that the compounds found within milk thistle work similarly to various diabetic medications by helping to improve insulin sensitivity and decrease blood sugar levels. Additionally, a recent analysis found that individuals who regularly consume milk thistle experience a significant reduction in their fasting blood sugar levels and hBA1c levels. In addition, studies indicate that the antioxidant and antiinflammatory properties of milk thistle are useful for reducing the risk of developing diabetic complications (e.g., kidney disease).

Regulating blood sugar levels is an important factor in weight management, and reducing the levels of blood sugar can be used to delay hunger. Milk thistle works to lower blood sugar levels, and these low levels help contribute to weight loss. As an individual taking milk thistle supplements experience fewer cravings for high sugar and high glycemic foods, there is a lower desire to consume high calorie, sugar filled, foods that are highly glycemic. This benefit helps overall health in addition to helping an individual lose weight.

Additionally, studies have indicated that berberine can facilitate in regulating blood sugar levels and obesity, which in turn, can help lower the risk of diabetes. Research indicates that berberine decreases insulin resistance (i.e., making it effective for lowering blood sugar levels), increases glycolysis inside cells, signals the liver to decrease glucose production, slows the breakdown of carbohydrates in the gastrointestinal tract, and increases the number of beneficial bacteria in the gastrointestinal tract. Moreover, berberine has been shown to provide a synergistic effect when combined with other diabetes medications, thus making it advantageous to help prevent diabetes and/or alleviate symptoms associated with diabetes.

Furthermore, berberine has been shown to assist in weight loss and weight management in several ways. For example, it has been demonstrated that berberine can target insulin resistance and help treat diabetes, increase the number of mitochondria and boost the metabolism (i.e., an increase in energy production resulting in weight loss), and induce brown fat breakdown while increasing overall fat breakdown. It has also been demonstrated that berberine can lower inflammation in fat and liver cells, thus improving thyroid function and reducing leptin resistance, treat gastrointestinal imbalances (due to the antibacterial and antifungal action of berberine), and boost the effect of other medications and supplements.

In addition, research has further indicated that berberine has a favorable effect on triglycerides and cholesterol levels, and has been shown to reduce apolipoprotein B. The addition of berberine in dietary supplements helps keep cholesterol levels in a healthy range. Berberine can help facilitate healthy levels of low-density lipoprotein (LDL) cholesterol, for example, by facilitating healthy ranges of LDL particle numbers and small density LDL. As such, berberine has been shown to have the ability to help maintain healthy cholesterol levels.

Diabetes tends to lower high-density lipoprotein (HDL) cholesterol and raise triglycerides and LDL cholesterol. This can lead to diabetic dyslipidemia, which can put an individual at risk for premature coronary heart disease and atherosclerosis. Studies have shown a link between insulin resistance, a precursor to type 2 diabetes, and diabetic dyslipidemia, atherosclerosis, and blood vessel disease. These conditions can develop even before diabetes is diagnosed, and thus it proves beneficial to prophylactically maintain healthy cholesterol levels in order to prevent health issues arising from late diagnosis of diabetes.

Furthermore, studies indicate that berberine has the ability to help regulate the expression of proprotein convertase subtilisin/kexin type 9 (PCSK9). Research further indicates the adenosine monophosphate-activated protein kinase (AMPK) activation by berberine results in increased nicotinamide adenine dinucleotide levels, mitochondria biogenesis, weight loss, and increased muscle fibers.

In addition to milk thistle and berberine, Ceylon cinnamon also has advantageous properties when taken as a supplement. Ceylon cinnamon includes various active compounds, such as, for example, cinnamaldehyde, eugenol, and hydroxycinnamaldehyde. Cinnamtannin B 1, a proanthocyanidin, found in Ceylon cinnamon has been demonstrated to improve fasting blood glucose levels in individuals with type 2 diabetes (insulin resistance). This effect is due to the compound stimulating insulin receptors in adipocytes (i.e., fat cells). The presence of cinnzeylanin and cinnceylanol increase gastric secretions and stimulates the appetite, which improves digestion and enhances the breakdown of fats. Moreover, researchers have shown that fat cells treated with cinnamaldehyde have positive implications. Studies indicated that there was a greater expression of genes and production of proteins that help with fat burning and lipid metabolism with the use of cinnamaldehyde. This demonstrates that Ceylon cinnamon helps fat cells burn energy, thus speeding up the process of weight loss, and can in turn assist in weight management.

Moreover, research has shown that Ceylon cinnamon can help lower blood sugar levels and fight diabetes by imitating the effects of insulin and increasing glucose transport into cells. Ceylon cinnamon also assists in lowering blood sugar levels by increasing insulin sensitivity, which makes insulin more efficient at transporting glucose into cells. Studies have indicated that Ceylon cinnamon increases insulin sensitivity immediately after consumption, with effects lasting over ten hours. Increased insulin sensitivity caused by Ceylon cinnamon can also occur when taken daily as part of a supplement.

Additionally, studies have indicated that chromium supplementation can help regulate healthy blood sugar levels. A significant number of chromium studies related to blood sugar levels have shown that chromium can normalize blood sugar levels, improve blood sugar utilization, and can decrease insulin requirements in individuals with glucose intolerance or insulin resistance. In a particular study, blood sugar responses to carbohydrate-rich meals demonstrated that the addition of chromium resulted in over a 20% reduction in blood sugar after the carbohydrate-rich meals. Thus, taking chromium with carbohydrate-rich foods can be an effective way to lower the glycemic index of particular carbohydrate-rich meals.

When blood sugar is low, the initiative to seek out sugars and starches is amplified in most individuals, leading to a tendency to overconsume calories. Research shows that taking chromium can significantly reduce carbohydrate cravings. Additionally, chromium supplementation helps to stabilize blood sugar levels and diminish the desire for carbohydrate-rich foods. Studies further indicate that supplementation of chromium reduces fat mass, while increasing lean body mass, which can lead to weight loss.

Furthermore, recent evidence indicates that chromium plays an important role in insulin signaling. One study examined the effects of chromium in mammals that were obese and insulin resistant. The results of this particular study clearly showed that mammals given additional chromium in their drinking water significantly improved glucose disposal rates and insulin-stimulated signaling in skeletal muscles. As such, this line of research indicated that extra chromium improves the insulin resistance normally present in these mammals. These findings are consistent with several studies showing improved glucose control in individuals with glucose intolerance and insulin resistance. As glycogen synthesis and protein synthesis are regulated by insulin signaling, adding chromium stimulates these processes in individuals who are insulin resistant.

In addition, studies have shown pyrroloquinoline quinone disodium (PQQ) alleviates fat-induced insulin resistance by increasing mitochondrial biogenesis in muscle cells, a byproduct that occurs similarly from exercise. Furthermore, PQQ has pro-oxidant potential by increasing hydrogen peroxide which can inhibit the PTP1B enzyme, a negative regulator of the insulin-signaling pathway, which increases insulin sensitivity. Additionally, studies on mammals have indicated that a deficiency in PQQ causes an approximate 10% decrease in metabolic rate. This indicates that extra PQQ supplementation could increase the metabolism, thereby assisting in weight management and/or weigh loss.

The above-mentioned studies have indicated that berberine, Ceylon cinnamon, chromium, milk thistle, and PQQ all provide support for weight management and/or weight loss, can help maintain healthy blood sugar levels, and can reduce the risk of diabetes. Furthermore, the studies described above indicate that berberine, Ceylon cinnamon, chromium, milk thistle, and PQQ can be beneficial, not only for reducing the risk of getting diabetes, but can help alleviate symptoms associated with diabetes and/or reduce health risks associated with diabetes.

As such, in various embodiments, a dietary supplement according to the present disclosure can include active ingredients, for example, berberine, Ceylon cinnamon, chromium, milk thistle, and PQQ. In some embodiments, the berberine can be berberine HCl, a berberine salt, or combinations thereof. In some embodiments, other forms of berberine are also envisioned. In some embodiments, the chromium can be chromium picolinate, chromium chloride, chromium aspartate, chromium amino acid chelate, chromium nicotinate (polynicotinate), glucose tolerance factor chromium, or combinations thereof. In some embodiments, Ceylon cinnamon can be substituted for other forms of cinnamon having advantageous health benefits. For example, Ceylon cinnamon can be substituted for *Cassia* cinnamon, Korintje cinnamon, Padang *Cassia* cinnamon, Indonesian cinnamon, Saigon cinnamon, Vietnamese *Cassia* cinnamon, Vietnamese cinnamon, Malabar cinnamon, Indian cinnamon, or combinations thereof.

In some embodiments, the dietary supplements of the present disclosure can include inactive ingredients, such as, for example, microcrystalline cellulose, sodium caprate, croscarmellose sodium, silicon dioxide, polyvinyl alcohol, polyethylene glycol, talc, magnesium stearate, titanium dioxide, carmine, various dyes (e.g., FD&C Blue #2 and FD&C Yellow #5), carnauba wax, or combinations thereof. In some embodiments, the inactive ingredients can include, without limitation anti-adherents, binders, coatings, colors, disintegrants, flavors, glidants, lubricants, preservatives, sorbents, sweeteners, vehicles, or combinations thereof. In some embodiments, the inactive ingredients can include texturizers, anti-caking agents, fat substitutes, emulsifiers, extenders, bulking agents, disintegrants, super-disintegrants, or combinations thereof.

In various embodiments, the dietary supplements of the present disclosure can be in the form of a pharmaceutical carrier, for example, a tablet, a capsule, a liquid, a suspension, a powder, a softgel, or the like. In some embodiments, the dietary supplements of the present disclosure can be in an extended release tablet, capsule, or the like.

Reference will now be made to more specific embodiments of the present disclosure and data that provides support for such embodiments. However, it should be noted that the disclosure below is for illustrative purposes only and is not intended to limit the scope of the claimed subject matter in any way.

Disclosed herein, is a formula that provides optimal amounts of active ingredients to meet the unique nutritional and dietary requirements to assist in weight management, promote weight loss, and help maintain healthy blood sugar levels. A particular example listing of active ingredients and amounts within the dietary supplement will be described in more detail below with respect to Table 1. Amounts are given based on serving size and, as will be appreciated by those of ordinary skill in the art, "mg" refers to "milligrams" and "mcg" refers to "micro grams". In typical embodiments, the daily dosage can be a single serving size, or up to three serving sizes per day. In some embodiments, the daily dosage can be one to two serving sizes up to three times daily. In some embodiments, the daily dosage can be two serving sizes three times daily. In some embodiments, the daily dosage can be two serving sizes two times daily. Additional embodiments allow for higher doses per day.

Table 1 below illustrates a particular example of a dietary supplement of the present disclosure. In this particular example, the dietary supplement includes the active ingredients of berberine in an amount of about 250 mg, Ceylon cinnamon in an amount of about 50 mg, chromium in an amount of about 50 mcg, milk thistle in an amount of about 25 mg, and pyrroloquinoline quinone disodium in an amount of about 5 mg.

TABLE 1

| Active Ingredient | Amount |
| --- | --- |
| Berberine HCl | 250 mg |
| Ceylon Cinnamon | 50 mg |
| Chromium (as Chromium Picolinate) | 50 mcg |
| Milk Thistle | 25 mg |
| Pyrroloquinoline Quinone Disodium (PQQ) | 5 mg |

As shown above in Table 1, in particular embodiments, the dietary supplement of the present disclosure can include berberine in an amount of about 250 mg, Ceylon cinnamon in an amount of about 50 mg, chromium in an amount of about 50 mcg, milk thistle in an amount of about 25 mg, and pyrroloquinoline quinone disodium in an amount of about 5 mg.

As Ceylon cinnamon can be substituted for other varieties of cinnamon, such as, but not limited to, *Cassia* cinnamon, Korintje cinnamon, Padang *Cassia* cinnamon, Indonesian cinnamon, Saigon cinnamon, Vietnamese *Cassia* cinnamon, Vietnamese cinnamon, Malabar cinnamon, Indian cinnamon, or combinations thereof, in some embodiments, the dietary supplement can include berberine in an amount of about 250 mg, cinnamon in an amount of about 50 mg, chromium in an amount of about 50 mcg, milk thistle in an amount of about 25 mg, and pyrroloquinoline quinone disodium in an amount of about 5 mg.

In some embodiments, the dietary supplement of the present disclosure can include berberine in a range of about 62.5 mg to about 437.5 mg, cinnamon in a range of about 12.5 mg to about 87.5 mg, chromium in a range of about 12.5 mcg to about 87.5 mcg, milk thistle in a range of about 6.25 mg to about 43.75 mg, and pyrroloquinoline quinone disodium in a range of about 1.25 mg to about 8.75 mg.

In some embodiments, the dietary supplement of the present disclosure can include berberine in an amount of about 62.5 mg, cinnamon in an amount of about 12.5 mg, chromium in an amount of about 12.5 mcg, milk thistle in an amount of about 6.25 mg, and pyrroloquinoline quinone disodium in an amount of about 1.2 mg.

In some embodiments, the dietary supplement of the present disclosure can include berberine in an amount of about 437.5 mg, cinnamon in an amount of about 87.5 mg, chromium in an amount of about 87.5 mcg, milk thistle in an amount of about 43.75 mg, and pyrroloquinoline quinone disodium in an amount of about 8.75 mg.

In some embodiments, the dietary supplement of the present disclosure can include berberine in a range of about 125 mg to about 375 mg, cinnamon in a range of about 25 mg to about 75 mg, chromium in a range of about 25 mcg to about 75 mcg, milk thistle in a range of about 12.5 mg to about 37.5 mg, and pyrroloquinoline quinone disodium in a range of about 2.5 mg to about 7.5 mg.

In some embodiments, the dietary supplement of the present disclosure can include berberine in an amount of about 125 mg, cinnamon in an amount of about 25 mg, chromium in an amount of about 25 mcg, milk thistle in an amount of about 12.5 mg, and pyrroloquinoline quinone disodium in an amount of about 2.5 mg.

In some embodiments, the dietary supplement of the present disclosure can include berberine in an amount of about 375 mg, cinnamon in an amount of about 75 mg, chromium in an amount of about 75 mcg, milk thistle in an amount of about 37.5 mg, and pyrroloquinoline quinone disodium in an amount of about 7.5 mg.

In some embodiments, the dietary supplement of the present disclosure can include berberine in a range of about 187.5 mg to about 312.5 mg, cinnamon in a range of about 37.5 mg to about 62.5 mg, chromium in a range of about 37.5 mcg to about 62.5 mcg, milk thistle in a range of about 18.75 mg to about 31.25 mg, and pyrroloquinoline quinone disodium in a range of about 3.75 mg to about 6.25 mg.

In some embodiments, the dietary supplement of the present disclosure can include berberine in an amount of about 187.5 mg, cinnamon in an amount of about 37.5 mg, chromium in an amount of about 37.5 mcg, milk thistle in an amount of about 18.75 mg, and pyrroloquinoline quinone disodium in an amount of about 3.75 mg.

In some embodiments, the dietary supplement of the present disclosure can include berberine in an amount of about 312.5 mg, cinnamon in an amount of about 62.5 mg, chromium in an amount of about 62.5 mcg, milk thistle in an amount of about 31.25 mg, and pyrroloquinoline quinone disodium in an amount of about 6.25 mg.

In some embodiments, the dietary supplement of the present disclosure can include berberine in an amount up to about 312.5 mg, cinnamon in an amount up to 62.5 mg, chromium in an amount up to about 62.5 mcg, milk thistle in an amount up to about 31.25 mg, and pyrroloquinoline quinone disodium in an amount up to about 6.25 mg.

In some embodiments, the dietary supplement of the present disclosure can include berberine in an amount up to about 375 mg, cinnamon in an amount up to 75 mg, chromium in an amount up to about 75 mcg, milk thistle in an amount up to about 37.5 mg, and pyrroloquinoline quinone disodium in an amount up to about 7.5 mg.

In some embodiments, the dietary supplement of the present disclosure can include berberine in an amount up to about 437.5 mg, cinnamon in an amount up to 87.5 mg, chromium in an amount up to about 87.5 mcg, milk thistle in an amount up to about 43.75 mg, and pyrroloquinoline quinone disodium in an amount up to about 8.75 mg.

In some embodiments, the dietary supplement of the present disclosure can include berberine in an amount up to about 500 mg, cinnamon in an amount up to 100 mg, chromium in an amount up to about 100 mcg, milk thistle in an amount up to about 50 mg, and pyrroloquinoline quinone disodium in an amount up to about 10 mg. In some embodiments, the berberine can be in an amount of about 500 mg.

In some embodiments, the dietary supplement of the present disclosure can include berberine in an amount up to about 562.5 mg, cinnamon in an amount up to 112.5 mg, chromium in an amount up to about 112.5 mcg, milk thistle in an amount up to about 56.25 mg, and pyrroloquinoline quinone disodium in an amount up to about 11.25 mg.

In some embodiments, the dietary supplement of the present disclosure can include berberine in an amount up to about 750 mg, cinnamon in an amount up to 150 mg, chromium in an amount up to about 150 mcg, milk thistle in an amount up to about 75 mg, and pyrroloquinoline quinone disodium in an amount up to about 15 mg.

In some embodiments, the dietary supplement of the present disclosure can include berberine in a range of about 250 mg to about 1500 mg, cinnamon in a range of about 50 mg to about 300 mg, chromium in a range of about 50 mcg to about 300 mcg, milk thistle in a range of about 25 mg to about 150 mg, and pyrroloquinoline quinone disodium in a range of about 5 mg to about 30 mg.

In some embodiments, the dietary supplement of the present disclosure can include berberine in an amount up to about 1500 mg, cinnamon in an amount up to 300 mg, chromium in an amount up to about 300 mcg, milk thistle in an amount up to about 150 mg, and pyrroloquinoline quinone disodium in an amount up to about 30 mg.

In view of the above, the present disclosure additionally relates to methods of use of the dietary supplements of the present disclosure. For example, in some embodiments, the method can include, without limitation, administering the dietary supplements of the present disclosure to a subject. Furthermore, the methods of the present disclosure can generally relate to, but are not limited to, managing weight, maintaining healthy blood sugar levels, preventing diabetes, alleviating symptoms associated with diabetes, or combinations of the same and like.

For example, in some embodiments, the methods of the present disclosure relate to a method of managing weight, maintaining healthy blood sugar levels, preventing diabetes, or alleviating symptoms associated with diabetes. In some embodiments, the method includes, without limitation, administering a composition to a subject. In some embodiments, the composition can be one or more of the dietary supplements described in detail herein. In a particular embodiment, the composition can include berberine in an amount of about 250 mg, Ceylon cinnamon in an amount of about 50 mg, chromium in an amount of about 50 mcg, milk thistle in an amount of about 25 mg, and pyrroloquinoline quinone disodium in an amount of about 5 mg.

As discussed above, Ceylon cinnamon can be substituted for other varieties of cinnamon, and as such, in some embodiments, the composition can include berberine in an amount of about 250 mg, cinnamon in an amount of about 50 mg, chromium in an amount of about 50 mcg, milk thistle in an amount of about 25 mg, and pyrroloquinoline quinone disodium in an amount of about 5 mg.

In some embodiments, the composition can include berberine in a range of about 62.5 mg to about 437.5 mg, cinnamon in a range of about 12.5 mg to about 87.5 mg, chromium in a range of about 12.5 mcg to about 87.5 mcg, milk thistle in a range of about 6.25 mg to about 43.75 mg, and pyrroloquinoline quinone disodium in a range of about 1.25 mg to about 8.75 mg.

In some embodiments, the composition can include berberine in an amount of about 62.5 mg, cinnamon in an amount of about 12.5 mg, chromium in an amount of about 12.5 mcg, milk thistle in an amount of about 6.25 mg, and pyrroloquinoline quinone disodium in an amount of about 1.2 mg.

In some embodiments, the composition can include berberine in an amount of about 437.5 mg, cinnamon in an amount of about 87.5 mg, chromium in an amount of about 87.5 mcg, milk thistle in an amount of about 43.75 mg, and pyrroloquinoline quinone disodium in an amount of about 8.75 mg.

In some embodiments, the composition can include berberine in a range of about 125 mg to about 375 mg, cinnamon in a range of about 25 mg to about 75 mg, chromium in a range of about 25 mcg to about 75 mcg, milk thistle in a range of about 12.5 mg to about 37.5 mg, and pyrroloquinoline quinone disodium in a range of about 2.5 mg to about 7.5 mg.

In some embodiments, the composition can include berberine in an amount of about 125 mg, cinnamon in an amount of about 25 mg, chromium in an amount of about 25 mcg, milk thistle in an amount of about 12.5 mg, and pyrroloquinoline quinone disodium in an amount of about 2.5 mg.

In some embodiments, the composition can include berberine in an amount of about 375 mg, cinnamon in an amount of about 75 mg, chromium in an amount of about 75 mcg, milk thistle in an amount of about 37.5 mg, and pyrroloquinoline quinone disodium in an amount of about 7.5 mg.

In some embodiments, the composition can include berberine in a range of about 187.5 mg to about 312.5 mg, cinnamon in a range of about 37.5 mg to about 62.5 mg, chromium in a range of about 37.5 mcg to about 62.5 mcg, milk thistle in a range of about 18.75 mg to about 31.25 mg, and pyrroloquinoline quinone disodium in a range of about 3.75 mg to about 6.25 mg.

In some embodiments, the composition can include berberine in an amount of about 187.5 mg, cinnamon in an amount of about 37.5 mg, chromium in an amount of about 37.5 mcg, milk thistle in an amount of about 18.75 mg, and pyrroloquinoline quinone disodium in an amount of about 3.75 mg.

In some embodiments, the composition can include berberine in an amount of about 312.5 mg, cinnamon in an amount of about 62.5 mg, chromium in an amount of about 62.5 mcg, milk thistle in an amount of about 31.25 mg, and pyrroloquinoline quinone disodium in an amount of about 6.25 mg.

In some embodiments, the composition can include berberine in an amount up to about 312.5 mg, cinnamon in an amount up to 62.5 mg, chromium in an amount up to about 62.5 mcg, milk thistle in an amount up to about 31.25 mg, and pyrroloquinoline quinone disodium in an amount up to about 6.25 mg.

In some embodiments, the composition can include berberine in an amount up to about 375 mg, cinnamon in an amount up to 75 mg, chromium in an amount up to about 75 mcg, milk thistle in an amount up to about 37.5 mg, and pyrroloquinoline quinone disodium in an amount up to about 7.5 mg.

In some embodiments, the composition can include berberine in an amount up to about 437.5 mg, cinnamon in an amount up to 87.5 mg, chromium in an amount up to about 87.5 mcg, milk thistle in an amount up to about 43.75 mg, and pyrroloquinoline quinone disodium in an amount up to about 8.75 mg.

In some embodiments, the composition can include berberine in an amount up to about 500 mg, cinnamon in an amount up to 100 mg, chromium in an amount up to about 100 mcg, milk thistle in an amount up to about 50 mg, and pyrroloquinoline quinone disodium in an amount up to about 10 mg. In some embodiments, the berberine can be in an amount of about 500 mg.

In some embodiments, the composition can include berberine in an amount up to about 562.5 mg, cinnamon in an amount up to 112.5 mg, chromium in an amount up to about 112.5 mcg, milk thistle in an amount up to about 56.25 mg, and pyrroloquinoline quinone disodium in an amount up to about 11.25 mg.

In some embodiments, the composition can include berberine in an amount up to about 750 mg, cinnamon in an amount up to 150 mg, chromium in an amount up to about 150 mcg, milk thistle in an amount up to about 75 mg, and pyrroloquinoline quinone disodium in an amount up to about 15 mg.

In some embodiments, the composition can include berberine in a range of about 250 mg to about 1500 mg, cinnamon in a range of about 50 mg to about 300 mg, chromium in a range of about 50 mcg to about 300 mcg, milk thistle in a range of about 25 mg to about 150 mg, and pyrroloquinoline quinone disodium in a range of about 5 mg to about 30 mg.

In some embodiments, the composition can include berberine in an amount up to about 1500 mg, cinnamon in an amount up to 300 mg, chromium in an amount up to about 300 mcg, milk thistle in an amount up to about 150 mg, and pyrroloquinoline quinone disodium in an amount up to about 30 mg.

In some embodiments, the composition can include any dietary supplement as disclosed herein. In some embodiments, the composition can include one or more of the dietary supplements as disclosed above. In some embodiments, the composition is administered orally. In some embodiments, the composition is administered once daily. In some embodiments the composition is administered twice daily. In some embodiments, the composition is administered three times daily. Additional embodiments allow for higher doses per day. In some embodiments, the composition is in a form of a pharmaceutical carrier that can include, but is not limited to, a tablet, a capsule, an extended release tablet, an extended release capsule, a liquid, a suspension, a powder, a softgel, or combinations thereof. In some embodiments, the composition is administered orally. In some embodiments, the composition is administered up to three times daily. In some embodiments, for example, the composition can be administered in the form of one to two tablets up to three times daily. In some embodiments, the composition can be administered orally via two tablets three times daily. In some embodiments, the composition can be administered orally via two tablets two times daily. In some embodiments, the composition is administered once daily in an extended release tablet or capsule. In some embodiments, the dietary supplement can have higher amounts of active ingredients for use with extended release tablets or capsules. For example, the dietary supplement can include berberine in an amount up to about 1500 mg, cinnamon in an amount up to 300 mg, chromium in an amount up to about 300 mcg, milk thistle in an amount up to about 150 mg, and pyrroloquinoline quinone disodium in an amount up to about 30 mg, as discussed above, and be utilized in an extended release tablet, capsule, or the like for single use daily.

Although various embodiments of the present disclosure have been described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially," "approximately," "generally," and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an," and other singular terms are intended to include the plural forms thereof unless specifically excluded.

What is claimed is:

1. A dietary supplement comprising:
   berberine is in a range of about 62.5 mg to about 437.5 mg;
   cinnamon is in a range of about 12.5 mg to about 87.5 mg;
   chromium is in a range of about 12.5 mcg to about 87.5 mcg;
   milk thistle is in a range of about 6.25 mg to about 43.75 mg; and
   pyrroloquinoline quinone disodium (PQQ) is in a range of about 1.25 mg to about 8.75 mg.

2. The dietary supplement of claim 1, wherein:
   the berberine is in a range of about 125 mg to about 375 mg;
   the cinnamon is in a range of about 25 mg to about 75 mg;

the chromium is in a range of about 25 mcg to about 75 mcg;

the milk thistle is in a range of about 12.5 mg to about 37.5 mg; and the PQQ is in a range of about 2.5 mg to about 7.5 mg.

3. The dietary supplement of claim 1, wherein:

the berberine is in a range of about 187.5 mg to about 312.5 mg;

the cinnamon is in a range of about 37.5 mg to about 62.5 mg;

the chromium is in a range of about 37.5 mcg to about 62.5 mcg;

the milk thistle is in a range of about 18.75 mg to about 31.25 mg; and the PQQ is in a range of about 3.75 mg to about 6.25 mg.

4. The dietary supplement of claim 1, wherein the berberine is about 250 mg.

5. The dietary supplement of claim 1, wherein the cinnamon is about 50 mg.

6. The dietary supplement of claim 1, wherein the chromium is about 50 mcg.

7. The dietary supplement of claim 1, wherein the milk thistle is about 25 mg.

8. The dietary supplement of claim 1, wherein the PQQ is about 5 mg.

9. The dietary supplement of claim 1, wherein the berberine is selected from the group consisting of berberine HCl, a berberine salt, and combinations thereof.

10. The dietary supplement of claim 1, wherein the berberine is berberine HCl.

11. The dietary supplement of claim 1, wherein the cinnamon is selected from the group consisting of Ceylon cinnamon, *Cassia* cinnamon, Korintje cinnamon, Padang *Cassia* cinnamon, Indonesian cinnamon, Saigon cinnamon, Vietnamese *Cassia* cinnamon, Vietnamese cinnamon, Malabar cinnamon, Indian cinnamon, and combinations thereof.

12. The dietary supplement of claim 1, wherein the cinnamon is Ceylon cinnamon.

13. The dietary supplement of claim 1, wherein the chromium is selected from the group consisting of chromium picolinate, chromium chloride, chromium aspartate, chromium amino acid chelate, chromium nicotinate, glucose tolerance factor chromium, and combinations thereof.

14. The dietary supplement of claim 1, wherein the dietary supplement is in a form of a pharmaceutical carrier selected from the group consisting of a tablet, a capsule, an extended release tablet, an extended release capsule, a liquid, a suspension, a powder, a softgel, and combinations thereof.

15. A dietary supplement comprising:

berberine in an amount of about 250 mg;

Ceylon cinnamon in an amount of about 50 mg;

chromium in an amount of about 50 mcg;

milk thistle in an amount of about 25 mg; and pyrroloquinoline quinone disodium (PQQ) in an amount of about 5 mg.

16. A method for managing weight, maintaining healthy blood sugar levels, preventing diabetes, or alleviating symptoms associated with diabetes, the method comprising: administering the dietary supplement of claim 1 to a subject in need thereof.

17. The method of claim 16, wherein:

the berberine is in a range of about 125 mg to about 375 mg;

the cinnamon is in a range of about 25 mg to about 75 mg;

the chromium is in a range of about 25 mcg to about 75 mcg;

the milk thistle is in a range of about 12.5 mg to about 37.5 mg; and the PQQ is in a range of about 2.5 mg to about 7.5 mg.

18. The method of claim 16, wherein:

the berberine is in a range of about 187.5 mg to about 312.5 mg;

the cinnamon is in a range of about 37.5 mg to about 62.5 mg;

the chromium is in a range of about 37.5 mcg to about 62.5 mcg;

the milk thistle is in a range of about 18.75 mg to about 31.25 mg; and the PQQ is in a range of about 3.75 mg to about 6.25 mg.

19. The method of claim 16, wherein the berberine is about 250 mg.

20. The method of claim 16, wherein the cinnamon is about 50 mg.

21. The method of claim 16, wherein the chromium is about 50 mcg.

22. The method of claim 16, wherein the milk thistle is about 25 mg.

23. The method of claim 16, wherein the PQQ is about 5 mg.

24. The method of claim 16, wherein the berberine is selected from the group consisting of berberine HCl, a berberine salt, or combinations thereof.

25. The method of claim 16, wherein the berberine is berberine HCl.

26. The method of claim 16, wherein the cinnamon is selected from the group consisting of Ceylon cinnamon, *Cassia* cinnamon, Korintje cinnamon, Padang *Cassia* cinnamon, Indonesian cinnamon, Saigon cinnamon, Vietnamese *Cassia* cinnamon, Vietnamese cinnamon, Malabar cinnamon, Indian cinnamon, and combinations thereof.

27. The method of claim 16, wherein the cinnamon is Ceylon cinnamon.

28. The method of claim 16, wherein the chromium is selected from the group consisting of chromium picolinate, chromium chloride, chromium aspartate, chromium amino acid chelate, chromium nicotinate (polynicotinate), glucose tolerance factor chromium, or combinations thereof.

29. The method of claim 16, wherein the dietary supplement is in a form of a pharmaceutical carrier selected from the group consisting of a tablet, a capsule, an extended release tablet, an extended release capsule, a liquid, a suspension, a powder, a softgel, and combinations thereof.

30. The method of claim 16, wherein the dietary supplement is administered orally.

31. The method of claim 16, wherein the dietary supplement is administered up to three times daily.

32. The method of claim 16, wherein the dietary supplement is administered orally via two tablets three times daily.

33. The method of claim 16, wherein the composition is administered orally via two tablets two times daily.

* * * * *